United States Patent [19]

Creekmore

[11] Patent Number: 4,812,118
[45] Date of Patent: Mar. 14, 1989

[54] PLACEMENT APPARATUS FOR LINGUAL AND BUCCAL BRACKETS

[76] Inventor: Thomas D. Creekmore, 362 Piney Point, Houston, Tex. 77024

[21] Appl. No.: 33,721

[22] Filed: Apr. 3, 1987

[51] Int. Cl.[4] .............................................. A61C 3/00
[52] U.S. Cl. ......................................... 433/2; 433/24; 433/53; 433/55; 433/61
[58] Field of Search ..................... 433/3, 2, 24, 49, 53, 433/55, 56, 61, 62, 63, 64, 65, 66, 72, 4, 153, 162

[56] References Cited

U.S. PATENT DOCUMENTS

| | | | |
|---|---|---|---|
| 2,613,440 | 10/1952 | Murray et al. | 433/55 |
| 2,669,780 | 2/1954 | Mann | 433/53 |
| 3,439,421 | 4/1969 | Perkowski | 433/3 |
| 3,686,762 | 8/1972 | Suiter | 433/3 |
| 3,738,005 | 6/1973 | Cohen | 433/3 |
| 3,871,098 | 3/1975 | Dean | 433/3 |
| 3,949,478 | 4/1976 | Schimhammer | 433/3 |
| 4,001,940 | 1/1977 | Cusato | 433/3 |
| 4,014,096 | 3/1977 | Dellinger | 433/3 |
| 4,017,972 | 4/1977 | Glenn | 433/53 |
| 4,035,919 | 7/1977 | Curato | 433/3 |
| 4,183,141 | 1/1980 | Dellinger | 433/3 |
| 4,360,341 | 11/1982 | Dellinger | 433/3 |
| 4,422,849 | 12/1983 | Diamond | 433/3 |
| 4,424,029 | 1/1984 | Maijer et al. | 433/3 |
| 4,431,409 | 2/1984 | Picard | 433/2 |
| 4,455,137 | 6/1984 | Diamond | 433/3 |
| 4,474,555 | 10/1984 | Diamond | 433/3 |
| 4,478,576 | 10/1984 | Maijer et al. | 433/3 |
| 4,494,931 | 1/1985 | Wildman | 433/3 |
| 4,501,554 | 2/1985 | Hickham | 433/3 |
| 4,523,540 | 6/1985 | Drisaldi et al. | 433/3 |
| 4,526,540 | 2/1985 | Dellinger | 433/24 |
| 4,551,096 | 11/1985 | Dellinger | 433/24 |

OTHER PUBLICATIONS

Torque/Angulation Reference Guide, by Cormco 1984/Division of Sybron Corporation.

Primary Examiner—John J. Wilson
Attorney, Agent, or Firm—Gunn, Lee & Jackson

[57] ABSTRACT

Apparatus for accurately placing orthodontic brackets on the lingual or labial surface of a model of a patient's maloccluded teeth in conjunction with an indirect bonding procedure or the like. A model support incorporates an immovable base forming a spherical surface segment which receives a complimentary spherical surface segment of a movable model platform thus providing for rotation of the platform in all planes of space about a centroid region. The maloccluded model is placed on the movable platform with a selected tooth thereof located at the central region of a sphere of which the spherical surface segments form a part. A tooth orienting template is releasably supported in fixed relation to the base structure and is selected according to the centrally positioned tooth of the model. The optimum position of the selected tooth relative to an optimum dental arch at the labial surface thereof is identified for bracket attachment to the labial surface. For attachment of brackets to the lingual surface of the tooth the labial bracket position is translated to the lingual surface of the tooth such that the lingual archwire slot position corresponds to the optimum labial archwire slot position. Bracket holding and release apparatus is employed to accurately position a bracket on the selected labial or lingual surface for temporary attachment thereof to the model. With all of the brackets attached to the model a conventional indirect bonding procedure may be carried out to accomplish bonding of the brackets to the enamel surfaces of the teeth of the patient.

36 Claims, 5 Drawing Sheets

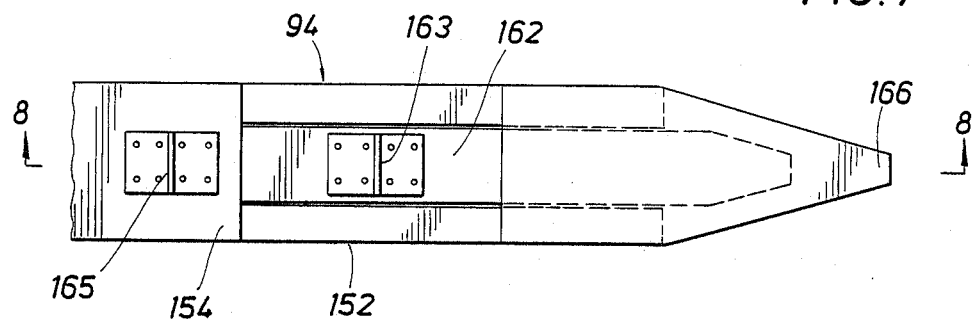
FIG. 7
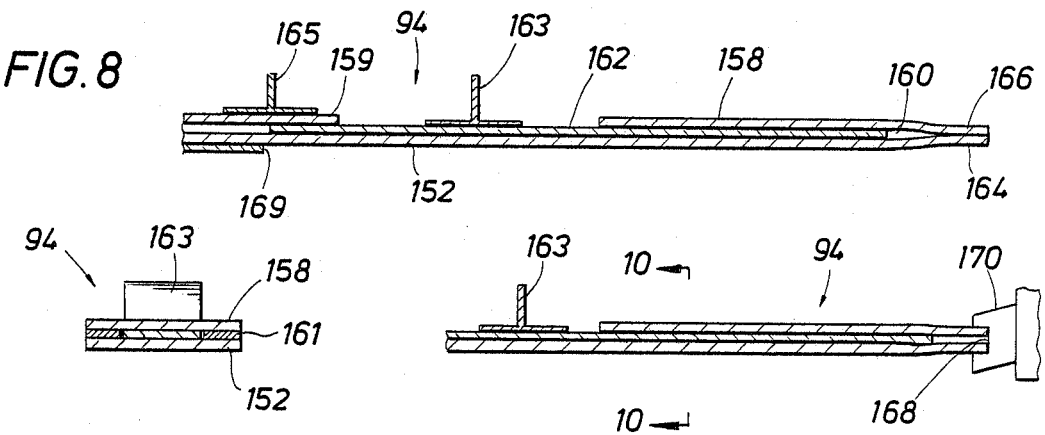
FIG. 8
FIG. 10
FIG. 9
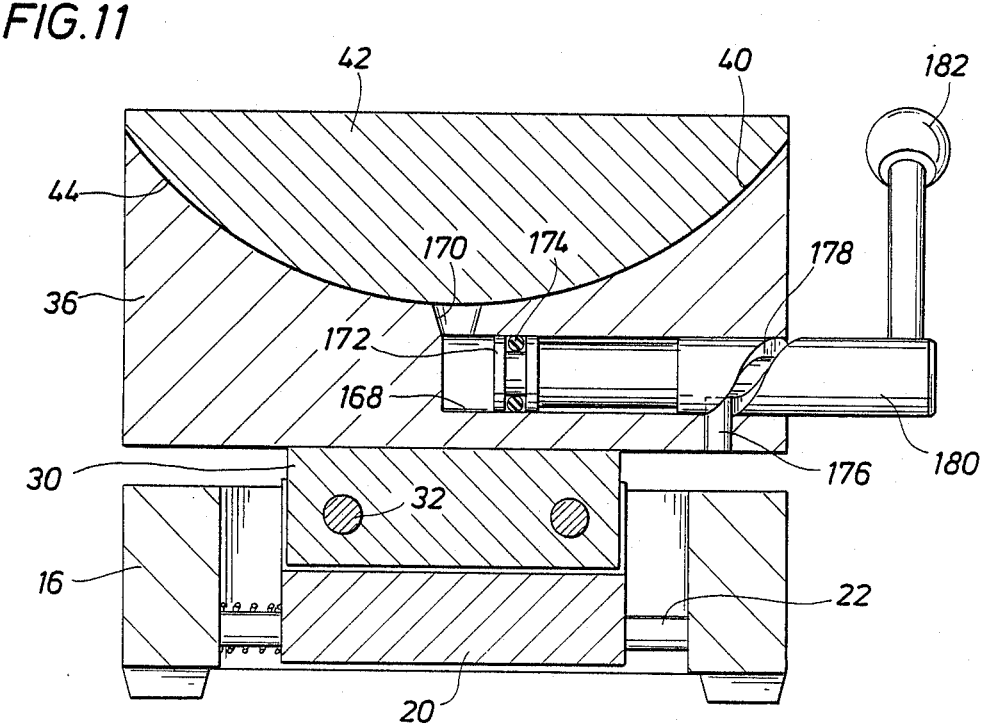
FIG. 11

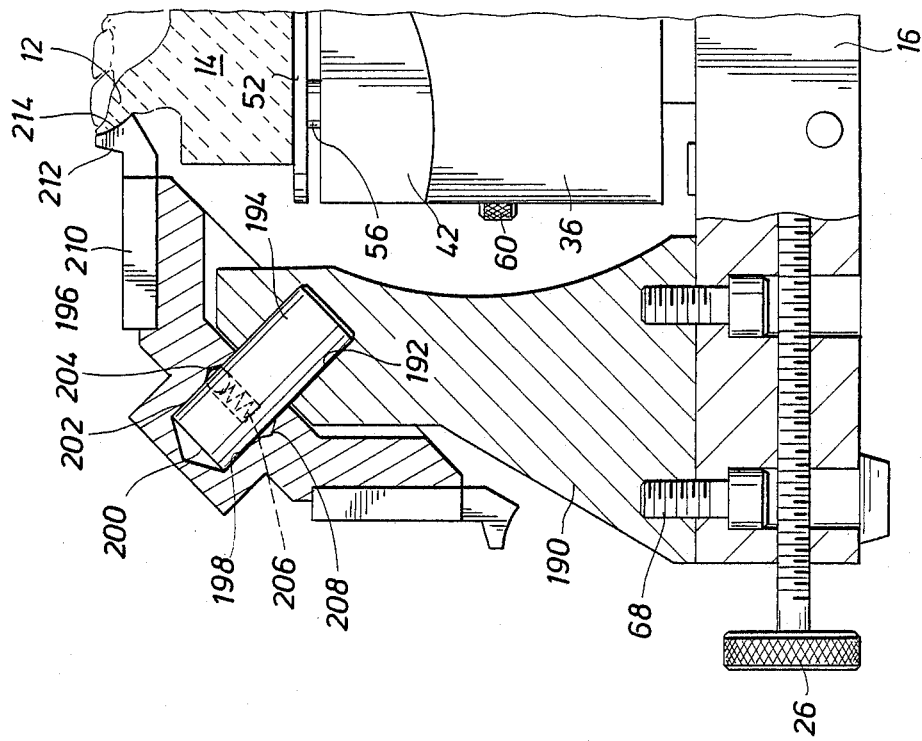
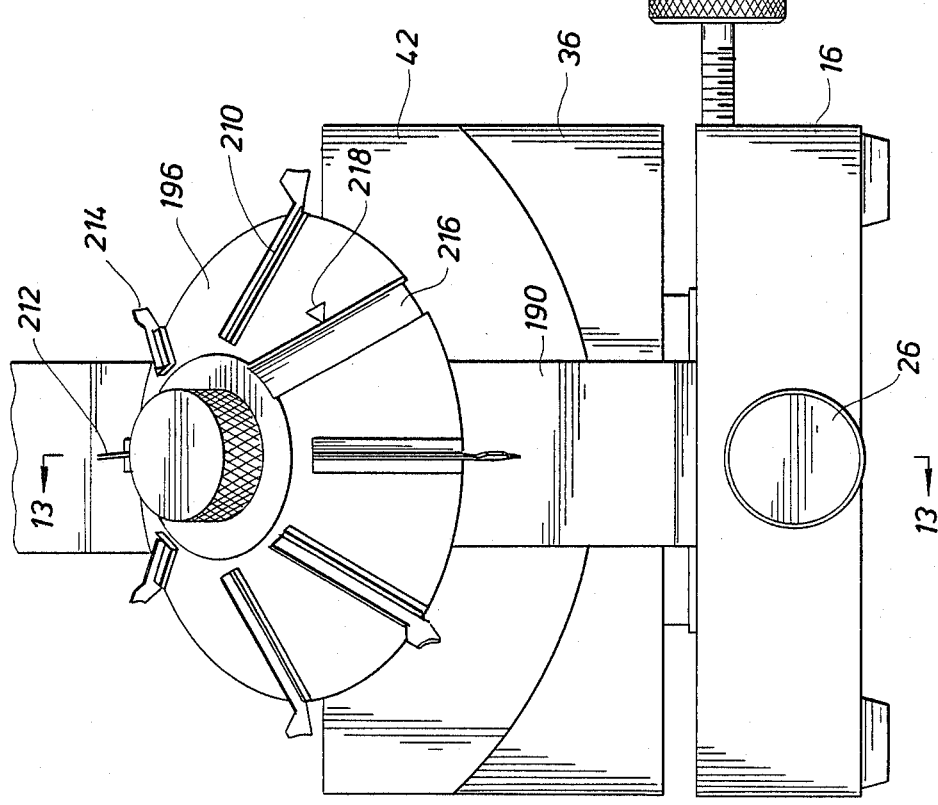

PLACEMENT APPARATUS FOR LINGUAL AND BUCCAL BRACKETS

FIELD OF THE INVENTION

This invention relates generally to indirect bonding procedures for bonding orthodontic brackets to the labial or lingual surfaces of the teeth of a patient undergoing orthodontic treatment. More specifically, the present invention relates to apparatus for precisely establishing archwire slot positions on the labial surfaces of the maloccluded teeth of a dental model. The apparatus provides for direct bonding of orthodontic brackets to the labial surfaces of the teeth of the model and also provides for translation of the spatial orientation of an imaginary labial archwire slot to appropriate positions relative to the lingual surfaces of the teeth. The apparatus also provides for accurate positioning of orthodontic brackets relative to the lingual surfaces for temporary attachment thereof by means of various adhesive materials such as water soluble cement, sugar based adhesive or bracket bonding material, etc. in readiness for mounting in conventional transfer trays, for indirect bonding of the brackets to the teeth of the patient.

BACKGROUND OF THE INVENTION

Bracket placement on the lingual surfaces of a patient's teeth for "straight wire" orthodontics is much more difficult than on the buccal surfaces of the teeth because it is the buccal surfaces of the teeth that are to be aligned to form an anatomically correct dental arch. While there are variations in buccal anatomy, the attachment of the brackets directly to the surfaces to be aligned negates most of the variations and produces excellent results with minimal archwire bending. Ease of manipulation to achieve quality finished orthondontic case is directly related to the quality and precision of bracket placement.

Conversely, the lingual surfaces of a patient's teeth are not the surfaces to be aligned. The lingual surfaces do not have a constant relationship with the buccal surfaces, therefore a constant appliance configuration for each tooth as in straight wire mechanics will not achieve consistent quality results from minimal archwire manipulation.

The indirect bonding technique for installation of orthodontic brackets requires two basic elements for success. First, an accurate measuring or placement device for the determination of the position of an archwire slot (includes tip, torque, rotation and height, and in/-out) on the buccal surface of each tooth which will position that surface ideally if the archwire slot were engaged with a full sized pre-formed archwire. This accurate measuring or placement device would be applicable to the straight wire concept of orthodontic therapy. Secondly, a jig or transfer device which would transfer the buccal archwire slot position to a parallel lingual slot position (includes tip, torque, rotation, in/-out and height) which could be attached to the lingual surface of the patient's teeth, i.e., the archwire slot on the lingual surface of the patient's teeth would be directly related to the buccal surface rather than to the lingual surface. It makes no difference whether the lingual archwire slot opens to the occlusal or to the lingual. Because of the accurate measurement of the buccal surfaces, the same bracket installation apparatus could be employed for very accurate buccal indirect bonding as well as lingual bonding. Variations in "prescriptions" used by different orthodontists could be accommodated simply by changing the torque and/or the angulation of the archwire slot. Variations in over corrections can also be accommodated for rotation, torque, angulation, etc.

Basically, it is desirable therefore to provide apparatus for installation of orthodontic brackets to the labial and facial surfaces of a patient's teeth or on the lingual surfaces of the patient's teeth with the positions of the archwire slots of the brackets being oriented in each case in relation to optimum archwire slot positioning on the buccal surfaces of the teeth.

SUMMARY OF THE INVENTION

It is a principal feature of the present invention therefore to provide novel apparatus for attachment of orthodontic brackets to the labial or lingual surfaces of the teeth of a maloccluded model wherein the brackets are positioned relative to an optimum buccal archwire slot position.

It is also a feature of this invention to provide novel apparatus for achieving accurate buccal and lingual placement of orthodontic brackets thus permitting efficient indirect bonding procedures for attachment of brackets to the teeth of a patient undergoing orthodontic treatment.

It is an even further feature of this invention to provide novel apparatus for installation of orthodontic brackets onto selected surfaces of the teeth of a maloccluded model, wherein the apparatus incorporates a mechanism for efficiently supporting orthodontic brackets in condition for cementing the brackets in the proper positions for accurate indirect bonding.

It is also an important feature of the present invention to provide a novel method for attachment of orthodontic brackets to the maloccluded teeth of a dental model in preparation for indirect bonding whether the teeth are intended for buccal or lingual attachment.

Briefly, the principles of the present invention are realized through the provision of a novel indirect bonding procedure whereby orthondontic brackets are applied to the maloccluded teeth of a dental model without necessitating arrangement of the teeth into an optimum arch form. Apparatus is provided herewith including a base structure having a model support in movable relation thereto and adapted for longitudinal and lateral movement relative to the base. The model support includes a model platform adapted for vertical movement relative to the model support. The movable model support forms a spherical surface segment of concave configuration which receives the convex spherical surface segment of a model orienting element. The model orienting element has a model support platform that is movable vertically relative to the model support element. The cooperative concave and convex spherical surfaces define a center point about which they are generated. This center point defines a centroid region of an imaginary sphere. A dental model on the model support platform is omnidirectionally positioned relative to all planes of space such that a tooth in question is located at or near the center point of this sphere, i.e. the centroid region, thus permitting ease of tooth positioning. A tooth guide or template is supported in fixed relation with the base and is utilized for proper orientation of each tooth of the model relative to an optimum center point which defines an archwire slot of an optimum arch form.

A bracket holder is provided which consists of two thin blades which collectively have a dimension smaller than the width of an archwire slot. A wedge member is movable between the blades and wedges the tips of the blades apart within the archwire slot to thus establish releasable frictional retention of the bracket by the bracket holder. The bracket holder blades will collapse upon movement of the wedge to its retracted position, thus releasing the bracket without disturbing its position on the model. The bottom of the bracket holder is oriented parallel in all planes of space to the imaginary labial archwire slot to which each tooth is aligned. Thus the bracket, while being held by the bracket holder with the lingual archwire slot optimally aligned to the labial surface, is releasably cemented to the model tooth.

The apparatus also employs a mechanism including a template for accurately positioning an orthodontic bracket on the buccal or lingual surface of a tooth and assuring that the archwire slot of the bracket is positioned relative to optimum buccal positioning of the optimum arch form. The template serves as a guide which enables the orthodontist to position orthodontic brackets on the maloccluded teeth, which brackets, when installed on the teeth of the patient, will apply tip, torque, height, rotation and in/out forces to the teeth for the movement of the teeth toward the finished positions thereof. The upper most surface of the template serves as a height guide. By aligning the upper guide surface with the incisal edge or buccal cusp tip of the teeth the bracket will be properly positioned for height. A guide blade of the template is angulated for the tip angle which is selected by the orthodontist for the particular tooth to which it relates. When the model is rotated to align the long axis of the tooth with the inclination of the template guide blade the bracket will be placed at the proper tip angle for the finished position of the tooth. The guide blade of the template is also provided with a concave curved end surface which matches the convex curvature of the tooth along the long axis of the tooth. The model is rotated during positioning until the convex labial or buccal surface of the tooth in question coincides closely with the curvature of the concave curved end surface. When the bracket is positioned on the tooth and cemented in place the archwire slot of the bracket will be at the preselected torque angle for finished positioning of the tooth.

Rotation control is also established by the apparatus in like fashion. The model is rotated through rotation of the omnidirectional model support until the labial or buccal surface of the tooth is perpendicular to the guide blade. To ensure that this perpendicular relationship is established a vertically oriented member with a horizontal surface located perpendicular to the guide blade is positioned so that the incisal edge of the tooth can be aligned with it. If the orthodontist requires "over rotation" such can be accomplished by rotating the tooth the desired "over correction" beyond the vertically oriented member. The bracket applied to the model tooth will then be properly positioned for rotation of the tooth to its finished overrotated position. The in/out position of each tooth is also individually controlled by the guide blade portion of the apparatus. The concave curved end surface of each bracket positioning template is at a specific distance from a guide stop or reference, thus permitting proper in-out location of each bracket relative to the tooth to which it relates. When subsequently attached to a patient's tooth, the bracket will be properly positioned to accomplish in or out tooth movement toward its preselected finished position.

The apparatus hereof achieves direct bracket location relative to the labial and buccal surfaces of the teeth of the model. The brackets then may be secured to the labial and buccal surfaces if desired. For lingual placement of the brackets the apparatus achieves effective translation of the labial bracket positions to the lingual surfaces of the maloccluded model. Thus, when the lingual brackets are installed on the lingual surfaces of the patient's teeth, the labial and buccal surfaces will be efficiently moved toward its finished position in the optimum arch form.

BRIEF DESCRIPTION OF THE DRAWINGS

In order that the manner in which the above recited advantages and features of the invention are attained and can be understood in detail a more particular description of the invention briefly summarized above may be had by reference to the specific embodiment thereof that is illustrated in the appended drawings, which drawings form a part of this specification. It is to be understood, however, that the appended drawings illustrate only typical embodiments of this invention and therefore are not to be considered limiting of its scope for the invention may admit to other equally effective embodiments.

IN THE DRAWINGS

Figure 1:
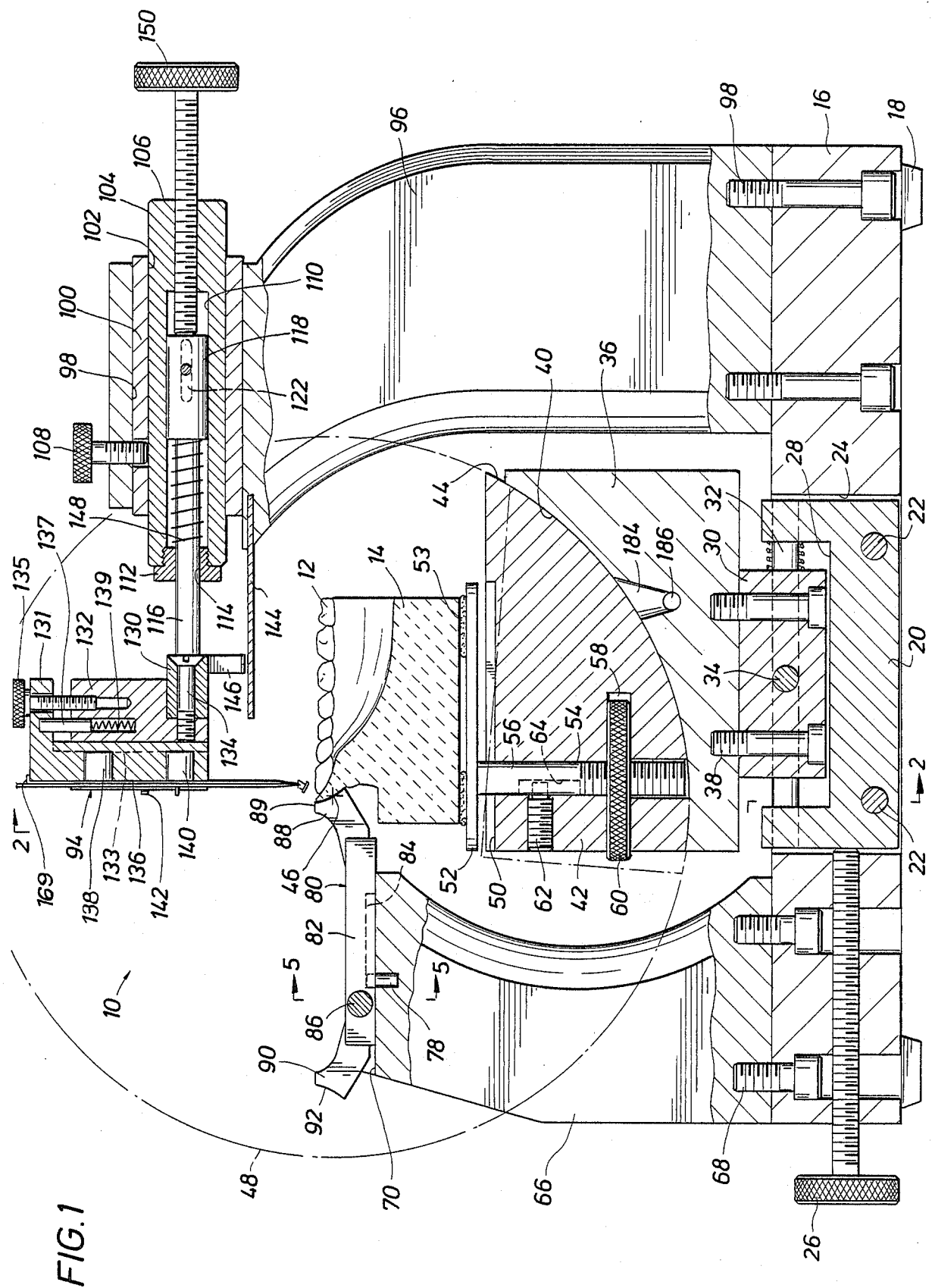
Figure 2:
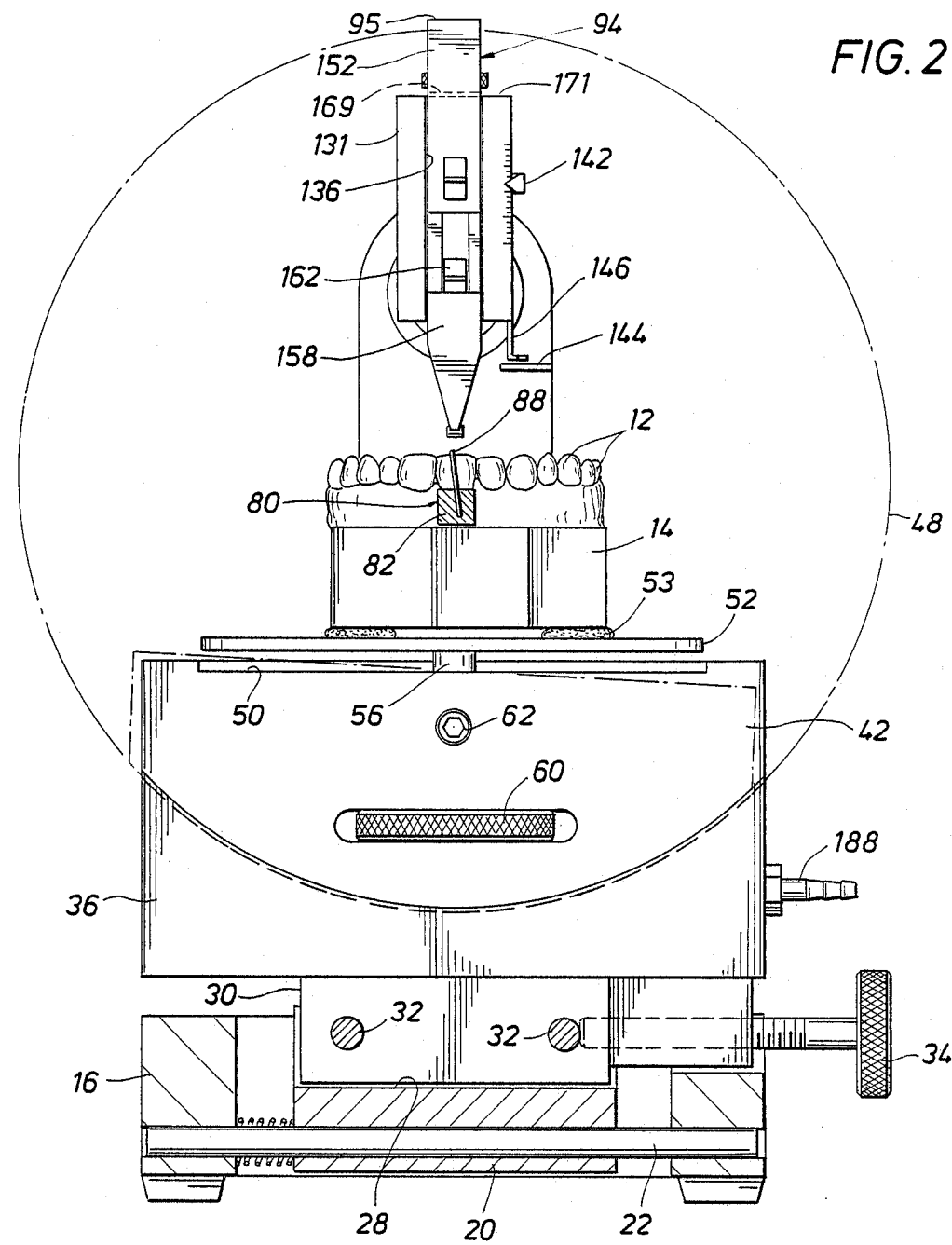
Figure 5:
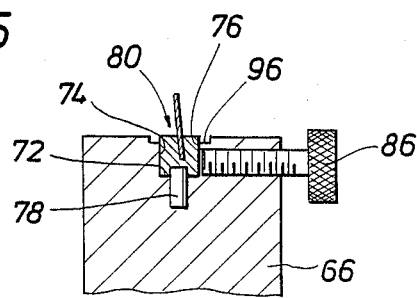
Figure 6:
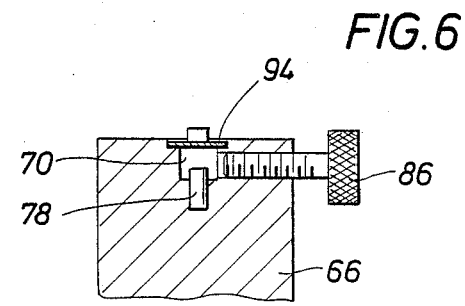
Figure 3:
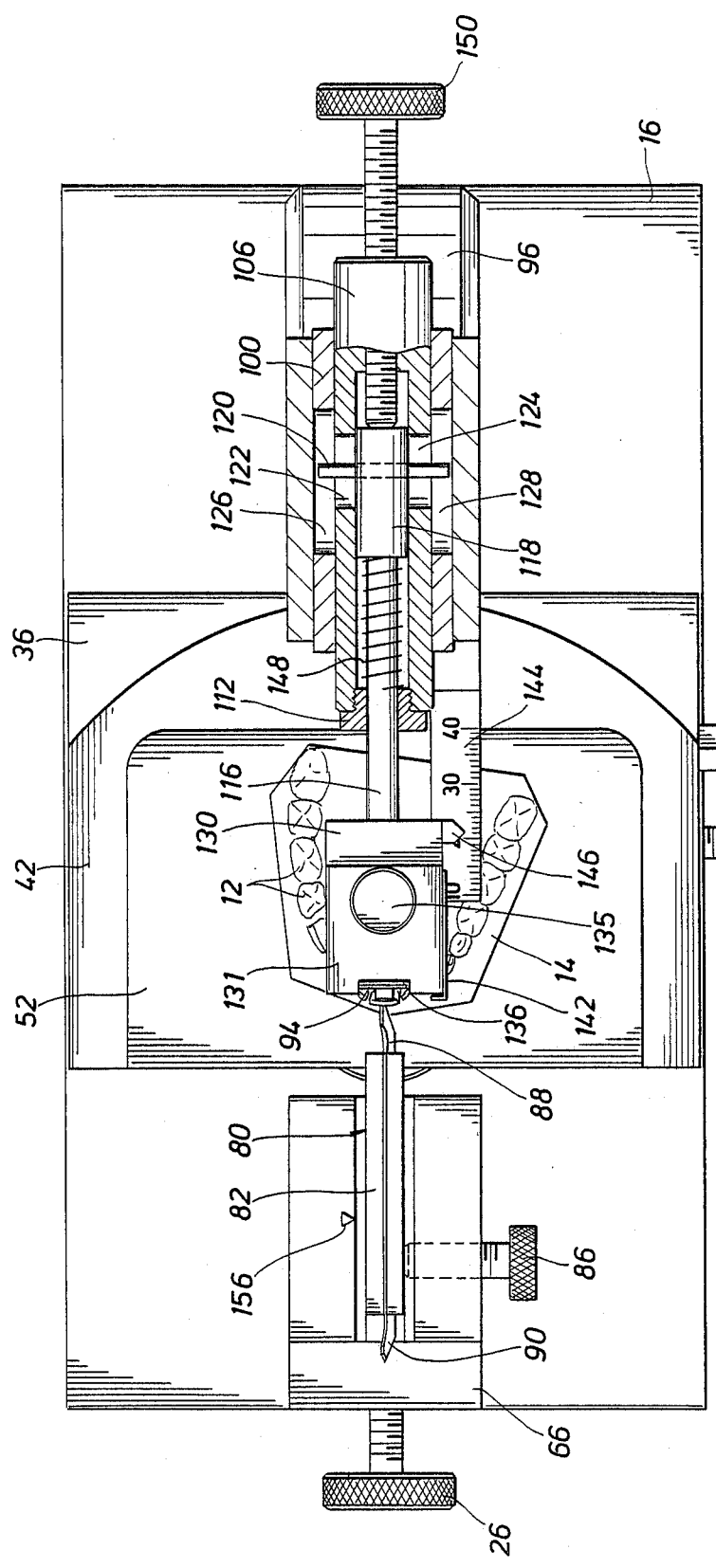
Figure 4:
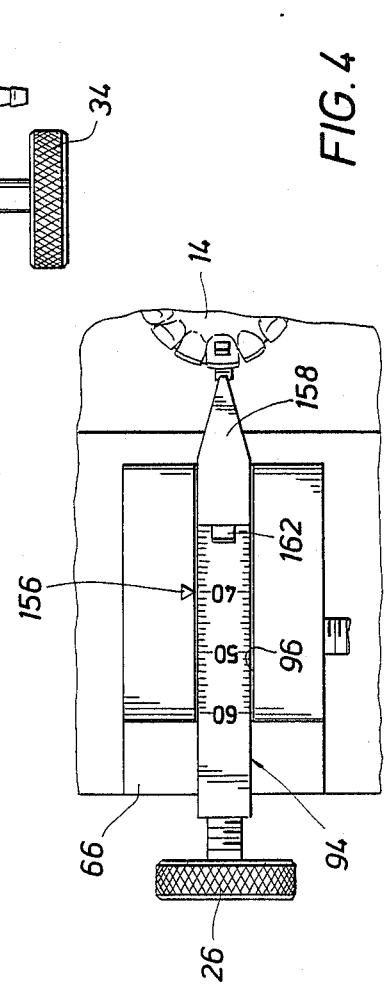

FIG. 1 is an elevational view with parts thereof broken away and shown in section, illustrating orthodontic bracket positioning apparatus constructed in accordance with the present invention;

FIG. 2 is a sectional view taken along line 2—2 of FIG. 1;

FIG. 3 is a plan view of the apparatus of FIGS. 1 and 2 with parts thereof broken away and shown in section;

FIG. 4 is a fragmentary plan view of the apparatus of FIG. 3 illustrating the bracket holding mechanism in position for buccal positioning of an orthodontic bracket relative to a tooth of the model;

FIG. 5 is a fragmentary sectional view of the apparatus taken along 5—5 of FIG. 1;

FIG. 6 is a fragmentary sectional view similar to that of FIG. 5 and illustrating the bracket positioning apparatus in the position shown in FIG. 4;

FIG. 7 is a partial view of the bracket supporting apparatus of FIGS. 4 and 6 which is enlarged to show structural details thereof;

FIG. 8 is a sectional view taken along line 8—8 of FIG. 7;

FIG. 9 is a fragmentary sectional view of the bracket holding and positioning apparatus of FIGS. 7 and 8, being shown in the expanded, gripping relation with an orthodontic bracket;

FIG. 10 is a sectional view taken along line 10—10 of FIG. 9;

FIG. 11 is a sectional view of bracket positioning structure similar to that of FIG. 1, and illustrating vacuum locking apparatus representing an alternative embodiment of this invention;

FIG. 12 is an elevational view of orthodontic bracket positioning apparatus representing an alternative embodiment of this invention; and FIG. 13 is a sectional view taken along line 13—13 of FIG. 12.

DETAILED DESCRIPTION OF PREFERRED EMBODIMENT

Referring now to the drwings and first to FIGS. 1, 2 and 3 bracket placement apparatus is shown generally at 10 which may be effectively utilized for placement of orthodontic brackets on the buccal or lingual surfaces of the maloccluded teeth 12 of a dental model 14. The apparatus 10 incorporates a base structure 16 having cushioned feet 18 enabling it to be supported on any flat surface such as the counter top of a dental laboratory. The bracket placement apparatus includes a model support mechanism which is movably associated with the base structure 16 and is adapted to support a maloccluded dental model and to provide for omnidirectional movement of the model so as to align respective teeth thereof with tooth guide or template apparatus to be discussed in detail hereinbelow. The model support mechanism incorporates a movable base structure 20 which is supported by lateral support bars 22 within a recess 24 defined by the base 16. The movable base 20 is therefore movable laterally along the parallel support bars 22. A base locking element 26, threadedly received by the base 16, is capable of engaging and locking the movable base 20 at any suitable position relative to the base. The movable base defines a recess 28 which receives a longitudinal guide block 30 supported by a pair of longitudinal guide bars 32 which are mounted in fixed relation to the movable base 20. A locking device 34 is threadedly received by the longitudinal guide block 30 and is capable of engaging and establishing a locking relationship with one of the longitudinal guide bars 32.

A support block 36 is secured by bolts 38 to the longitudinal guide block 30 and is therefore movable longitudinally along with the guide block 30 as well as being movably laterally along with guide block 30 and movable base 20. The mechanism incorporating movable base 20 and longitudinal guide block 30 permits the support block 36 to have both longitudinal and lateral movement relative to the base 16.

In order to permit efficient positioning of the model 14 in order that the maloccluded teeth thereof may be properly oriented for lingual or buccal bracket placement it is desirable to provide apparatus for achieving omnidirectional movement of the model. It is also desirable to permit proper and accurate positioning of the model with a minimum number of adjustments, thereby permitting the bracket location and placement activity to be accomplished efficiently. It was envisioned that if selected teeth of the maloccluded model could be placed as near as practical to the center of a fairly large sphere and if the model could be subjected to circular components of movement relative to the centroid region of the sphere, the dental model could be quite efficiently positioned without significant trial and error. Accordingly, with this spherical positioning concept in mind, the support block 36 is formed to define a concave spherical surface segment 40. A model support structure 42 is provided having a convex spherical surface segment 44 provided thereon. Spherical surface segments 40 and 44 are generated about the center point 46 of a sphere 48, a majority of which is imaginary. The model support 42 merely rests upon the concave spherical surface and thus is omnidirectionally movable relative to the support block. The model support therefore achieves omnidirectional movement of a particular tooth of the model 14 which is being oriented for bracket placement. The model support is capable of being locked to the support block 36 by a vacuum locking system or by other means as explained below.

The model support 42 defines a recess 50 which receives a model support platform 52. To temporarily secure the model on the model support platform a quantity of suitable tacky or sticky substance 53 is applied to the model support platform. The model is then positioned in contact with the substance 53 as shown in FIG. 1 to temporarily secure it in immovable relation with the support platform. The model is repositioned on the support platform such that each tooth is near the center of the imaginary sphere. Fine adjustments are then accomplished as indicated below to achieve precise positioning of each tooth with respect to the guide template for that particular tooth. The model support defines a bore 54 receiving platform jack post 56 to which the support platform 52 is fixed. A transverse recess 58 formed by the model support receives a thumb wheel type drive nut 60 which establishes threaded engagement with a lower section of the jack post 56. Upon rotation of the drive nut 60 the jack post 56 is moved downwardly or upwardly within the bore 54 to thus induce upward or downward movement to the support platform 52. To prevent the support platform from rotating relative to the model support 42 a guide pin 62 retained by the model support engages within a guide groove 64 formed within the jack post. With lateral and longitudinal movement provided by the movable base 20 and the longitudinal guide block 30, with omnidirectional circular positioning of the model being provided by the movable relationship of the model support to the model support block and with vertical movement of the model being accomplished by the jack mechanism of the model support platform, a selected tooth of the model can be accurately induced with all necessary components of movement for accurate positioning of the tooth relative to the center of the sphere and to a tooth positioning guide or template located at the centroid region of the sphere. Tooth positioning movement of the model support relative to the model support block is located at a sufficient distance from the center of the sphere that large components of movement at the spherical surfaces 40 and 42 will result in minute components of tooth movement. The tooth can be quickly and accurately positioned to receive its bracket.

A tooth orienting pedestal 66 is secured to the base 16 by means of bolts 68 and defines a guide positioning slot structure 70 at the upper portion thereof. The structure of configuration of the positioning slot 70 is more readily apparent from FIGS. 5 and 6. A major portion of the positioning slot is of generally rectangular form defined by a bottom surface 72 and parallel side surfaces 74 and 76. A guide pin 78 is received by the pedestal 66 and projects into the guide slot 70.

A plurality of guide elements or templates are provided as shown generally at 80. Each of the guide elements incorporates an elongated rectangular body portion 82 which is receivable in close fitting relation within the guide slot 70 as shown in FIG. 5. The rectangular body 82 defines an elongated recess 84 which receives the guide pin 78 and thus permits longitudinal movement of the guide member 80 within the guide slot. The ends of the recess 84 serve as stop surfaces so that the guide members can be accurately positioned within the guide slot. A locking element 86 is threadedly received by the pedestal 66 as shown in FIGS. 5 and 6 and is positionable to engage the body 82 and lock the guide member within the positioning slot 70. At the end portions of the rectangular body 82 is provided at least one and preferably a pair of guide blades or templates 88 and 90 which are appropriately configured for respective teeth of the dental model. For example guide blade 88 may be provided for the right central incisor of the model while blade 90 may be provided for the left central incisor of the model. Curved guide surfaces or edges 92 at respective ends of the guide blades 88 and 90 are appropriately configured for the labial or buccal surface configuration of particular teeth of the model. These concave curved guide surfaces provide for proper positioning of brackets for application of torque forces to the teeth. When the guide element 80 is positioned with an end surface of slot 84 in engagement with the positioning pin 78 the respective guide surface 92 of the selected guide blade or template is properly positioned relative to an optimum buccal arch form. The blade portion of the guide element may also be utilized for proper orientation of the teeth of the model to achieve tip, height and in-out movement of the patient's teeth as well. Through manipulation of the model 14 a particular tooth thereof may be brought into accurate registry with the curved guide surface 92 in the manner shown in FIG. 1. The model can be raised or lowered by rotating the manually operable jack drive nut 60 for adjusting the height of the tooth relative to the upper edge of the guide blade. After this has been done the individual tooth of the model is properly positioned for attachment of an orthodontic bracket thereto.

There is a guide element such as that shown at 80 with a particular guide blade 88–90 which is designated for each tooth of the matrix of teeth defined by the model. A particular guide blade will therfore relate to a specific tooth. Therefore, to accurately position a buccal or lingual orthodontic bracket on a particular tooth of the model, the guide or template member for that particular tooth is positioned within the slot 70 of the tooth orienting pedestal 66. The body member 82 of the guide element is then moved toward the tooth to the extent permitted by engagement of the guide pin 78 with an end surface of the slot 84. When such positioning has been accomplished, the center of the curved guide surface 92 will be positioned at the center of the sphere from which the model support member 42 is generated. The locking element 86 is then tightened to secure the guide member 80 in immovable relation with respect to the tooth orienting pedestal 66, the base member 16 and the position translation pedestal 96. Location of the curved surface 92 of the guide blade 88 in a particular relation with respect to the center point of the sphere determines the inout position of that particular tooth in an optimum arch form. Each guide blade will have a particular relationship with respect to the center point of the sphere thus permitting the in-out relationships of the various teeth to be accurately positioned with respect to an optimum arch form. For proper control of the height of each tooth, the incisal edge of anterior teeth or the buccal cusp tips of posterior teeth are brought into aligned registry with the upper guide surface 89 of the guide blade member 88. The position of each height alignment surface 89 of a particular blade will be established to ensure accurate height positioning of each tooth. Each guide blade 88–90 of the guide template 80 is angulated in the manner shown in FIGS. 2, 3 and 5 to thus control the tip angle of respective teeth. For example upper central teeth may be angulated at a tip angle of 5°, upper lateral teeth may be angulated at a tip angle of 7° and cuspids may be angulated at a tip angle of 11°. Various tip angles are of course selected by the orthodontist according to appropriate treatment for the individual involved. Each guide blade will therefore be angulated at an appropriate tip angle as preselected by the orthodontist for each of the teeth. The maloccluded model is then appropriately positioned by omnidirectional manipulation such that the long axis of the tooth in question is brought into proper alignment or registry with the angulated guide blade in the manner shown in FIGS. 2. With the model so positioned and stabilized, the orthodontic bracket is then installed on the buccal or lingual surface of the model in the manner discussed above. When that particular tooth of the patient has been moved to its finished position by the labial or lingual archwire, the buccal surface of the tooth will be properly positioned with respect to the preselected arch form.

As mentioned above, the guide blade 88–90 of the template 80 is provided with a curved surface 92 which conforms to the curvature of the labial or buccal surface of a respective tooth. Proper positioning of the model 14 includes appropriate omnidirectional movement to bring the labial or buccal surface of the tooth in question into accurate registry with the curved surface 92 of the guide blade in the manner shown in FIG. 1. When a precise match has been established with the concave curved surface 92 of the guide blade and the convex curved surface of the respective tooth then the bracket, when installed on the labial or lingual surface of the model will be appropriately positioned for application of torque forces to the tooth in question. Thus, the labial or lingual bracket, interacting with the edgewise archwire will move the tooth in question to a finished position bringing its labial or buccal surface into optimum relation with the arch form.

Rotation control of the respective teeth during orthodontic treatment is established by positioning of the teeth of the model such that the convex curved surface thereof is perpendicular to the horizontal axis of the guide blade at its central point. Since it is difficult to accomplish accurate alignment of a curved surface with respect to the inclined guide blade, a vertically oriented guide member may be effectively employed. The bracket holder 94 when properly positioned in the groove 136 of member 132 defines an upper surface 195 that is positioned horizontally. The bracket holder 94 may be reversed within the slot 136 thus positioning the edge 95 adjacent the incisal edge of the tooth in question. The end surface 95 of the bracket holder thus effectively serves as a guide. The incisal edge of the tooth in question is aligned with the horizontal surface 95. Since the horizontal surface 95 is perpendicular to the horizontal axis defined by the guide blade, the labial or buccal surface of the tooth in question will be properly perpendicular to the horizontal axis of the guide blade. Thus, when the archwire interacts with the labial, buccal or lingual surfaces of the teeth of the patient, appropriate rotation forces will be developed causing the tooth to rotate to a finished position properly aligning the labial or buccal surface with respect to a desired arch form. In the alternative a tooth rotation guide may simply take the form of an elongated strip having transverse flanges at each end. One of the flanges establishes a guide edge for incisors and the other flange establishes a guide edge for bicuspids.

For attachment of an orthodontic bracket to the labial or buccal surface of the tooth a bracket support and bracket holder 94 is positioned in the shallow groove 96 defining the outer portion of the slot 70. The bracket holder 94, which is shown in detail in FIGS. 7-10 and described hereinbelow, fits tightly within the shallow groove portion 96 and accurately positions a buccal bracket relative to a selected position the tooth in question. When the tooth is properly aligned with respect to the guide surface 92 the selected point of bracket application is in the central region of the tooth and at or near the center point 46 of the sphere 48. A quantity of water soluble cement, bonding material or other suitable material is employed to secure the buccal bracket temporarily to the buccal surface of the tooth in accordance with conventional indirect bonding procedure.

For attachment of orthodontic brackets to the lingual surface of the tooth in question the bracket holder 94 will itself be positioned in the manner shown in FIG. 1. The bracket holder, which is discussed in detail hereinbelow in connection with FIGS. 7-10, includes a gripping portion receivable within the archwire slot of the bracket and thus provides support for the bracket during positioning relative to the tooth. Again, the bracket is cemented to the tooth by a water soluble cement in accordance with conventional indirect bonding technique.

For accurate positioning and bonding of orthodontic brackets to the lingual surfaces of the maloccluded teeth of the model 14, accurate alignment of the buccal surface of a tooth of the model with respect to a guide blade of the guide element 80 is accomplished. The buccal bracket position must then be accurately translated to the lingual surface of the tooth in question. Thus the position of the archwire slot of the bracket, whether opening toward the occlusal or to the lingual, is translated from the buccal surface of the tooth. When the lingual archwire mechanically interacting with the lingual brackets has moved the teeth to their finished positions the buccal surfaces of the teeth will have assumed proper position relative to an optimum buccal arch form.

For accurate positioning of a lingual orthodontic bracket relative to the lingual surface of the tooth the apparatus may conveniently take the form illustrated in FIGS. 1-3. A position translation pedestal 96 is secured to the base 16 by means of bolts 98 and thus is in fixed relation to the base 16 and to the tooth orienting pedestal 66. The upper portion of the position translation pedestal defines a bore 98 receiving a guide sleeve 100 in fixed relation therein. The guide sleeve 100 forms an inner cylindrical guide surface 102 receiving the outer cylindrical surface 104 of a coarse adjustment member 106 in close fitting relation therewith. A lock member 108 is threadedly received by the upper portion of the positio translation pedestal and is adapted to engage and establish locking relation with the coarse adjustment member 106. The coarse adjustment member in turn defines an internal blind bore forming an internal guide surface 110. The outer portion of the blind bore is enclosed by means of a bushing member 112 which is threadedly received by the coarse adjustment member 106. The bushing 112 defines a cylindrical bearing surface 114 which provides a guiding function for a bracket positioning shaft 116. At the internal end of the bracket positioning shaft is provided a guiding enlargement 118 which is received in close fitting relation with the inner cylindrical guide surface 110. To maintain proper orientation of the bracket positioning shaft 116 a shaft orienting pin 120 extends transversely through the enlarged portion 118 of the shaft 116 with opposed end portions thereof received by guide slots 122 and 124 of the coarse adjustment member 106 and opposed slots 126 and 128 defined by the sleeve member 100. Thus, the bracket positioning shaft 116 and the coarse adjustment member 106 are prevented from any degree of rotation. These components simply move linearly relative to the upper portion of the position translation pedestal.

A connector block 130 which is fixed to the free extremity of the bracket positioning shaft 116 is secured to a bracket holder block 132 by means of screw members 134. A vertically movable bracket holder slide 131 is received within a dove-tail slot 133 of the bracket holder block 132 and is vertically movable by a positioning screw member 135. The slide is accurately guided by the dovetail slot and by a guide pin 137. The guide pin is spring loaded by a spring 139 to apply a continuous force against the slide to compensate for thread looseness and permit accurate slide positioning. The bracket holder slide 131 forms a vertically oriented recess 136 which receives the bracket holder 94 in positively aligned and oriented relation with respect to the bracket holder slide. Although the bracket holder may be secured to the bracket holder slide in any suitable fashion, the embodiment illustrated in FIGS. 1-3 accomplishes magnetic retention of the bracket holder. Upper and lower magnets 138 and 140 are secured within the bracket holder slide 131 and provide magnetic retention of the bracket holder. The position of the bracket holder relative to the bracket holder slide 131 is accurately controlled by a stop element 169 shown in FIG. 2. Reference indicia is provided on the bracket holder slide 131 and the position of the bracket holder is adjusted vertically until a reference element 142 on the bracket holder block 132 registers with the reference indicia. For control of forward and backward movement of the shaft 116 and thus forward and backward positioning of the bracket supported by the bracket holder an indicia bearing member 144 is secured to the upper portion of the position translation pedestal 96. A reference member 146 extending from the connector block 130 is provided with a mark that may be brought into registry with appropriate indicia on member 144. Through proper positioning of the reference mark relative to the indicia on member 144 the position of the bracket supported by the bracket holder may be effectively oriented in appropriately translated relation with respect to the buccal surface of the tooth.

For fine adjustment of the bracket positioning shaft 116 a compression spring member 148 surrounding the shaft is positioned with its respective ends bearing against the bushing member 112 and the enlargement 118. The compression spring urges the bracket positioning shaft 116 toward the right as shown in FIG. 1. A fine adjustment screw member 150 is threadedly received by the coarse adjustment member 106 and is rotatable clockwise or counter clockwise for appropriate positioning of the shaft 116 relative to the coarse adjustment member. Thus, the bracket holder includes means for both coarse and fine adjustment to enable the user to simply and efficiently achieve optimum positioning of the lingual bracket.

Referring now to FIGS. 7-10 the bracket holder shown generally at 94 comprises an elongated strip member 152 which may be provided with indicia in the form of measurement marks 154 which enable the bracket holder to be accurately positioned relative to the reference mark 156 of FIG. 4 for accurate positioning of orthodontic brackets in the buccal mode. To the elongated strip member 152 is secured a pair of spaced shorter strip members 158 and 159 which cooperate with spacer strips 161 and with strip member 152 to define a pocket or receptacle 160 receiving a locking slide member 162. The slide 162 forms a transversely projecting member 163 and the short strip 159 has a transversely projecting fixed member 165. To retract the slide 162 a squeezing force is applied to member 163 and 165 by the user which causes the slide to move to the left as shown in FIG. 8. The strip members 152 and 158 form bracket gripping ends 164 and 166 respectively which are bent toward one another such that the end portions in the collapsed positions thereof are ordinarily in substantial contact in the manner shown in FIG. 8. The ends 164 and 166 have a combined thickness which is less than the width of the archwire slot of the bracket to be supported thereby. This feature enables the ends 164 and 166 to be easily inserted into the archwire slot of an orthodontic bracket. The strip members 152 and 158 are composed of a resilient material such as stainless spring steel and are thus movable from the collapsed position shown in FIG. 8 to the expanded position shown in FIG. 9 upon movement of the locking slide 162 to a locking position near the ends 164 and 166. In the expanded position shown in FIG. 9 the bracket supporting ends 164 and 166 will have been expanded to the locking position where the thickness defined by the spaced ends 164 and 166 provides for efficient frictional engagement of the end portions of the bracket holder within the archwire slot 168 of the orthodontic bracket 170. In this manner the orthodontic bracket is efficiently supported by frictional engagement with the end portions of the bracket holder thus permitting the bonding base of the bracket to be accurately and efficiently positioned relative to the selected surface of the tooth to which the bracket is to be attached. After the bracket has been brought into engagement with the temporary cement either before or after curving of the cement, it is necessary to release the bracket without disturbing its position. This is efficiently accomplished simply by squeezing the members 163 and 165 and thus moving the locking slide member 162 to the left as shown in FIGS. 8 and 9, or upwardly in the position shown in FIG. 1 thus extracting it from its locking or expanding position between the end portions 164 and 166. The end portions will move from the expanded position shown in FIG. 9 to the collapsed position shown in FIG. 8, thus releasing frictional engagement with the opposed side surfaces of the archwire slot 168. The bracket holder is then easily moved linearly away from the archwire slot without disturbing the position of the bracket.

The bracket holder also provides a stop member 169 which engages the upper shoulder 171 of the bracket holder slide 131 to limit further downward movement and achieve precise positioning of the bracket holder device relative to the bracket holder slide.

The bracket holder 94 defines straight edges at the upper and lower ends thereof, the edge of greater length being shown at 95. For bracket placement to achieve efficient rotational control either of the upper or lower edges of the bracket holder are used as a guide. Obviously, if the longer edge 95 is so employed the bracket holder position will be inverted from the position shown in FIG. 2. The straight edge of the bracket holder and a portion of the tooth of the model are brought into juxtaposed relation. The position of the model is then adjusted to accurately align the selected tooth of the model with the straight edge. When the bracket is then positioned on the tooth for proper torque, tip, in-out and height it will also be properly positioned to impart rotation to the tooth.

After the model 14 has been properly positioned through appropriate manipulation of the movable base, the connector and support blocks 30 and 36, the model support element 42 and the support platform 52, it will be desirable to secure the model in an immovable position to accomplish efficient bracket placement. According to the present invention one suitable means for stabilizing the model 14 may conveniently take the form of a vacuum induced locking system which releasably fixes the model support element 42 relative to the support block 36. This feature is shown in FIGS. 1 and 2 and is shown by way of an alterantive embodiment in FIG. 11. As shown in FIG. 11 the support block 36 defines a piston bore 168 which is in communication with the concave spherical surface segment 40 of the support block by means of a connecting passage 170. A piston member 172 is movably disposed within the piston chamber and is sealed by means of an annular sealing member 174. When the piston member moves to the right as shown in FIG. 11 the volume of the piston chamber increases and thus develops a negative pressure or vacuum which is communicated via the connecting passage 170 to the spherical interface between spherical surface segments 40 and 44. This vacuum condition causes the model support 42 to be seated tightly against the spherical surface 40 of the support block thus inducing frictional locking of the support block. When the piston moves to the left the volume of the piston chamber diminishes thus increasing the pressure that is communicated to the spherical interface between surfaces 40 and 44. In this unlocked condition the model support element 42 is readily movable relative to the support block.

Linear movement of the piston is accomplished according to FIG. 11 by a rotary/linear actuator mechanism. An actuator pin 176 received by the support block 36 extends slightly into the piston bore 168 and is received by a helical slot 178 formed in an actuator extension 180 of the piston. The actuator extension is provided with an operating handle 182 which may be manually rotated to accomplish linear and rotary movement of the piston member for vacuum locking and unlocking.

Accoding to the vacuum locking and unlocking system illustrated in Figs.1 and 2. A connector passage 184 is provided which communicates a vacuum passage 186 with the interface between spherical surface segments 40 and 44. The vacuum passage 186 extends through the support block and terminates at an external connector element 188 shown in FIG. 2. The external connector is adapted to receive a vacuum tube coupled with a suitable source of vacuum, not shown. The vacuum source may be a vacuum pump or a vacuum system such as is commonly found in dental offices Referring to FIGS. 12 and 13 an alternative embodiment of the present invention is illustrated which includes a turret apparatus for supporting a plurality of tooth guide elements which may be selectively positioned relative to selected teeth of a dental model. A major portion of the apparatus of FIGS. 12 and 13 may be substantially identical to features set forth in the apparatus of FIGS. 1-3. Accordingly, like parts are illustrated by like reference numerals.

A tooth orienting pedestal 190 is secured in immovable relation to the base 16 by means of connector bolts 68. The tooth orienting pedestal defines a blind bore 192 within which is fixed a turret shaft 194. A turret member 196 forms a blind bore 198 within which is received the outer extremity 200 of the turret shaft 194. The surface forming the blind bore 198 functions as a bushing surface establishing a precise, rotatable fitting relation with the outer cylindrical surface 202 of the turret shaft. For accurate positioning of the turret member relative to the turret shaft a ball detent locking member 204 is received within a transverse bore of the turret shaft 194 and is urged outwardly by means of a compression spring 206. The ball detent is receivable within selected ones of a plurality of detent recesses 208.

The turret member 196 is provided with a plurality of tooth guide elements 210 which are in fixed relation with the turret. Each of the guide elements is provided with a guide blade or template 212 forming an appropriate guide surface for a particular tooth. When a particular guide element is positioned in guiding relation with the model 14 the selected tooth or teeth to which the guide surface relates may be precisely positioned by appropriate manipulation of the position of the model in the manner discussed above. When so positioned the position of the model is stabilized such as by energization of the vacuum locking system to permit cementing of a bracket to the buccal or lingual surface of the tooth. For labial application of an orthodontic bracket the turret 196 is provided with a bracket positioning receptacle 216 which receives the bracket holder 94. With the model stablized the turret is rotated to align the bracket positioning receptacle 216 with a selected tooth of the model. The bracket holder is inserted within the receptacle 216 and is appropriately positioned relative to a reference mark 218 to thus accurately establish positioning of the archwire slot relative to the tooth of the model. For lingual application of brackets, the bracket holder 94 is again utilized but is positioned in substantially vertical manner as shown in FIG. 1.

Through employment of the apparatus of the present invention and through utilization of the novel method incorporated herein, lingual or buccal orthondontic brackets may be efficiently submitted to the maloccluded teeth of a dental model in preparation for an indirect bonding technique. Through utilization of the present apparatus, orthodontic brackets may be selectively positioned on the buccal or lingual surfaces of the teeth of the model. Moreover, where lingual brackets are attached to the model the optimum buccal archwire position relative to the buccal surfaces of the teeth is translated to the lingual surfaces of the teeth. This feature permits the archwire slot positions of the lingual brackets, whether opening toward the occlusal or lingual, to be accurately related to the buccal surfaces of the teeth. Thus, when final tooth movement is accomplished by means of the lingual archwire the buccal surfaces of the teeth will form an optimum dental arch. Accordingly, it is respectfully submitted that the orthodontic bracket installation apparatus and the method of its use is capable of accomplishing all of the features hereinabove set forth together with other features which are inherent from a description of the apparatus itself. It will be understood that certain combinations and subcombinations are of utility and may be employed without reference to other features and subcombinations. The scope of this invention is intended to be limited only by the scope of the appended claims and is not limited by the specific embodiments shown and described herein.

What is claimed is:

1. Apparatus for selectively placing edgewise orthodontic brackets on the lingual and labial surfaces of a model of a patient's maloccluded teeth and in relation to an ideal dental arch plane, comprising:
   (a) base means
   (b) tooth orienting means projecting from said base means and establishing optimum labial and buccal surface positions of the maloccluded teeth of a dental model to permit archwire induced force application to orthodontic brackets on a patient's teeth to establish optimum tip, rotation, torque, in-out and height movement of selected teeth relative to a preselected dental arch;
   (c) model support means being omnidirectionally movable for selectively positioning individual teeth of said model relative to said tooth orienting means, said model support means defining a spherical surface segment having a centroid region, said tooth orienting means being located in said centroid region and said spherical surface segment of said model support means being movable about said centroid region for positioning selected teeth of said model in said centroid region; and
   (d) bracket support means for individually supporting edgewise orthodontic brackets and being movable to position said edgewise orthodontic brackets such that the archwire slots thereof are located at selected lingual and labial positions relative to said preselected dental arch for attachment thereof to respective teeth of said model.

2. Apparatus as recited in claim 1 wherein said model support means is omnidirectionally rotatable at said spherical surface segment in all planes of space about said centroid region near which the labial or buccal surface a selected tooth of said model is to be located.

3. Apparatus as recited in claim 1, wherein said bracket support means is selectively positionable for location of orthodontic brackets relative to the labial and buccal surfaces of the teeth of said model.

4. Apparatus as recited in claim 1, wherein said bracket support means is selectively positionable for location of orthodontic brackets relative to the lingual surfaces of the teeth of said model.

5. Apparatus as recited in claim 1, wherein said bracket support means is positionable for selective location of orthodontic brackets relative to the labial, buccal and lingual surfaces of the teeth of said model.

6. Apparatus as recited in claim 1 wherein said tooth orienting means comprises:
   (a) an orienting pedestal extending upwardly from said base means and being fixed relative thereto, said orienting pedestal defining a guide receptacle; and
   (b) a plurality of teeth orienting guide template devices each defining at least one guide blade having a tooth positioning end and being selectively positionable in removable assembly within said guide receptacle and positioning said guide blade thereof with a tooth positioning end located at a predetermined position relative to said base means and said centroid region.

7. An apparatus as recited in claim 6, wherein:

said guide blade is angulated at a tip angle designated for the tooth to which it relates and forms a concave curved end surface establishing a bracket position for application of torque force to said tooth, said curved end surface being positioned for in-out tooth movement, said guide blade further defining an upper guide surface for registry with said model for proper height location of an orthodontic bracket on said tooth of said model.

8. Apparatus as recited in claim 6, wherein:
   (a) guide positioning means is provided at said guide receptacle; and
   (b) said selected tooth orienting guide template device is linearly movable from a tooth orienting position to a retracted position relative to said guide positioning means.

9. Apparatus as recited in claim 8, wherein:
   (a) said guide receptacle is an elongated guide slot;
   (b) said guide positioning means is a stop member extending from said orienting pedestal into said elongated guide slot;
   (c) said selected tooth orienting guide template device defines spaced stop surfaces respectively engagable with said stop member at said tooth orienting position and said retracted position; and
   (d) means for locking a selected one of said tooth orienting guide template devices at selected positions within said elongated guide slot.

10. Apparatus as recited in claim 9, wherein said tooth orienting guide template devices each comprise:
    (a) an elongated guide bar having precision interfitting relation with said elongated guide slot; and
    (b) guide blade means extending from opposite ends of said guide bar, each of said guide blade means defining a guide for specific ones of said teeth of said model.

11. Apparatus as recited in claim 1, including:
    (a) base means;
    (b) an orienting pedestal extending upwardly from said base means;
    (c) a turret being rotatably positioned on said orienting pedestal and being selectively positionable at a plurality of rotary positions; and
    (d) a plurality of tooth orienting devices being supported at angularly spaced positions on said turret, each of said tooth orienting devices having a guide template member establishing a preselected tooth position upon selected tooth orienting positioning thereof.

12. Apparatus as recited in claim 1, wherein said model support means comprises
    (a) a support block being movably connected to said base means and forming a concave spherical surface segment; and
    (b) a model support defining a convex spherical surface segment being receivable in interfitting relation with said concave spherical surface segment and forming a model support platform for releasably receiving said model.

13. Apparatus as recited in claim 12, including locking means for selectively locking said partially spherical model support in fixed relation with said support block.

14. Apparatus as recited in claim 13, wherein said locking means comprises:
    means for applying a vacuum condition between said concave spherical surface and said partially spherical model support for vacuum induced friction locking of said partially spherical model support to said support block.

15. Apparatus as recited in claim 14, wherein said means for applying a vacuum condition comprises:
    (a) means forming a variable volume vacuum chamber in communication with said concave spherical surface; and
    (b) means selectively increasing the volume of said variable volume vacuum chamber and developing a vacuum at the interface between said concave spherical surface and said partially spherical model support.

16. Apparatus as recited in claim 12 wherein said support block establishes longitudinal and lateral components of positioning movement relative to said base means for longitudinal and lateral positioning of said model support element and said model relative to said tooth orienting means, said convex spherical surface segment of said model support element being omnidirectionally movable and relative to said concave spherical surface segment of said support block for orientation of a selected tooth of said model relative to said tooth orienting means.

17. Apparatus as recited in claim 16, including:
    means establishing a vertical component of movement for said model support platform.

18. Apparatus as recited in claim 12, wherein said model support means includes:
    (a) a model support platform in vertically movable relation with said model support means; and
    (b) means for imparting vertical movement to said model support platform relative to said model support.

19. Apparatus as recited in claim 18, wherein said means for imparting vertical movement to said model support platform comprises:
    (a) a jack bore being formed by said model support;
    (b) a jack post extending from said model support platform and having a threaded end received within said jack bore; and
    (c) a positioning nut being rotatably received by said spherical model support and establishing threaded engagement with said jack post, whereby rotation of said positioning nut induces vertical movement of said jack post and model support platform.

20. Apparatus as recited in claim 1, including:
    (a) a translation pedestal extending from said base means;
    (b) a bracket support arm being movably assembled to said translation pedestal; and
    (c) a bracket holder being movably supported by said bracket support arm and adapted to engage within the archwire slot of an edgewise orthodontic bracket such that said archwire slot is positioned in lingual translation with said ideal dental arch plane.

21. Apparatus as recited in claim 20, wherein said bracket holder comprises:
    (a) a pair of blade elements having end portions establishing a combined width less than the spacing of the parallel side surfaces of an edgewise archwire slot; and
    (b) a locking element being disposed between said pair of blade elements and being movable from a retracted position where said blade elements are easily inserted into and removed from said archwire slot and a locking position where said blade elements are spread to establish friction retention with the parallel side surfaces of an edgewise archwire slot.

22. Apparatus as recited in claim 21, wherein:
(a) an orienting pedestal extends from said base means; and
(b) said bracket holder is releasably connected to said bracket support arm and is adapted for releasable connection to said translation pedestal for positioning of orthodontic brackets relative to the labial surfaces of the teeth of said model.

23. Apparatus as recited in claim 20, wherein said bracket support arm comprises:
(a) support arm guide means being fixed to said translation pedestal;
(b) coarse adjustment means being received in movable relation with said support arm guide means and capable of being locked in fixed relation to said support arm guide means; and
(c) fine adjustment means being movably connected to said coarse adjustment means and being manually controllable to impart fine linear adjustment to said support arm shaft.

24. Apparatus as recited in claim 20, wherein:
(a) magnetic support means is secured to said bracket support arm and establishes a generally vertically oriented guide surface; and
(b) said bracket holder is magnetically secured by said magnetic support means with said blade elements positioned to orient an edgewise lingual orthodontic bracket with the archwire slot thereof selectively opening toward the occlusal or lingual.

25. A method of positioning orthodontic brackets on the lingual surfaces of the maloccluded teeth of a model of the teeth of a dental patient, comprising:
(a) providing a model support establishing an imaginary sphere forming a centroid region near the center of said imaginary sphere for support of said model with a selected tooth thereof located at said centroid regions;
(b) positioning a tooth guide template device having a guide element thereon with a guide end surface thereof located at said centroid region of said imaginary sphere and establishing a position relative to an optimum labial dental arch;
(c) orienting said model by omnidirectional movement thereof including rotation thereof about the center of said imaginary sphere such that a selected tooth of the model is positioned in aligned registry with said guide element including rotation and that the labial surface, incisal edge and cusp tip of said selected tooth is brought into accurate registry with said guide element to establish an optimum archwire slot position on the labial and buccal surface of each tooth, said orienting translating said archwire slot position to the lingual surface of said tooth for lingual bracket placement;
(d) positioning an orthodontic bracket with the archwire slot thereof located at said optimum archwire slot position;
(e) securing said orthodontic bracket to said tooth; and
(f) repeating method steps (a) through (e) for other teeth of said model.

26. The method of claim 25, including:
(a) translating said optimum archwire slot position from said labial and buccal surface to the lingual surface of said tooth; and (b) said securing comprising cementing said orthodontic bracket to said lingual surface of said tooth with a temporary cement or bonding material.

27. The method of claim 25, wherein said orienting includes:
positioning said model by omnidirectional rotational movement relative to said centroid region such that said tooth is precisely located relative to said guide element.

28. A method for selectively positioning orthodontic brackets on the labial and lingual surfaces of the teeth of a maloccluded dental model, comprising:
(a) providing a model support establishing an imaginary sphere forming a center point having a centroid region immediately thereabout for support of said model with a selected tooth thereof located at said centroid region;
(b) positioning guide template means defining guide means for establishing a labial archwire slot position, said guide template having tooth alignment means for aligning a selected tooth of said model for torque, tip, height, rotation, and in-out positions;
(c) for each selected tooth of said maloccluded dental model, orienting said model by omnidirectional movement with respect to all planes of space including rotation of said model about said centroid region at which said guide means and said selected tooth are located for alignment of said selected tooth with said guide means to thus establish an archwire slot position relative to said selected tooth;
(d) supporting an orthodontic bracket with the bonding base thereof exposed for attachment to said selected tooth;
(e) positioning said orthodontic bracket with the archwire slot thereof in registry with said archwire slot position;
(f) attaching said bonding base of said orthodontic bracket to said selected tooth; and
(g) releasing said orthodongic bracket.

29. The method of claim 28, including translating said archwire slot position form the labial-buccal surface of said selected tooth to the lingual surface thereof and positioning said orthodontic bracket for attachment to said lingual surface.

30. A bracket holder for supporting an edgewise orthodontic bracket defining spaced parallel surfaces that cooperate to form an archwire slot adapted to receive an edgewise archwire in close fitting relation therebetween, comprising:
(a) a pair of locking elements being in fixed assembly along a portion of the length thereof and having parallel flat locking end portions establishing a combined width less than the spacing of said spaced parallel surfaces of an edgewise orthodontic bracket; and
(b) a locking slide element being disposed between said pair of locking elements and being linearly movable from a retracted position where said parallel flat locking end portions of said locking elements are easily inserted into and removed from said archwire slot and a locking position where said locking slide element forces said parallel flat locking end potions of said blade elements to a spaced locking position to establish friction retention with said spaced parallel surfaces of said archwire slot.

31. A bracket holder as recited in claim 30, wherein:

said locking slide element is a flat locking blade interposed between said locking elements with an expansion portion thereof disposed for linear locking and interlocking movement between said pair of locking elements.

32. A bracket holder as recited in claim 30, wherein:
(a) said pair of locking elements cooperate to define slot means therebetween; and
(b) said locking slide element is disposed for linear movement within said slot means.

33. A bracket holder as recited in claim 32, wherein: said pair of locking blade elements and said flat locking slide element each define manually engageable elements enabling manual movement of said locking slide element to said locking and retracted positions relative to said pair of locking elements.

34. An apparatus for location of orthodontic brackets relative to the teeth of the model of a patient's maloccluded teeth, comprising:
(a) a model support adapted to support said model for omnidirectional movement;
(b) a tooth orienting pedestal being disposed in substantially fixed relation with said model support and forming an elongate template receptacle slot and a template stop;
(c) at least one template device being receivable within said template receptacle slot and engaging said template stop to define a fixed optimum tooth position, said template device having at least one guide blade extending therefrom and being angulated relative to said template device to identify the desired tip angle of the tooth and also identifying bracket positions for torque, in-out movement and height location and defining the anatomical configuration of a particular tooth of said model, said template device further providing for translation of labial bracket positions to lingual bracket positions, said template device being removably secured within said template receptacle slot such that said guide blade is located at a predetermined position for a particular tooth relative to a properly occluded arch form; and
(d) said template device being movable between an orienting position where template device engages said template stop and locates said guide blade at said predetermined position and a retracted position where said guide blade is moved away from said predetermined position.

35. The improvement of claim 34, wherein:
(a) said tooth orienting pedestal defines an elongated slot having said template stop in association therewith;
(b) said template device is positionable for linear guided movement within said elongated slot and defines an elongated stop receptacle; and
(c) a template stop is fixed to said tooth orienting pedestal within said elongated slot and is received within said elongated stop receptacle of said template device, said template stop limiting movement of said template device between said orienting position and said retracted position.

36. the improvement of claim 34, wherein:
(a) said tooth orienting pedestal defines a generally horizontal bracket holder slot; and
(b) a bracket holder for engaging within the archwire slot of an edgewise orthodontic bracket is receivable within said bracket holder slot for location of said orthodontic bracket relative to the labial or buccal surfaces of the teeth of said model.

* * * * *